United States Patent [19]

Jäger

[11] 3,954,817

[45] May 4, 1976

[54] PROCESS FOR THE MANUFACTURE OF PERFLUOROALKYLMETHYLENE-CARBOXYLIC ACIDS

[75] Inventor: Horst Jäger, Bettingen, Switzerland

[73] Assignee: Ciba-Geigy Corporation, Ardsley, N.Y.

[22] Filed: Feb. 15, 1974

[21] Appl. No.: 442,951

[30] Foreign Application Priority Data
Mar. 5, 1973 Switzerland................ 3186/73

[52] U.S. Cl................ 260/408; 260/539 R
[51] Int. Cl.²........................ C07C 51/16
[58] Field of Search............... 260/539 R, 408

[56] References Cited
UNITED STATES PATENTS 3,255,228   6/1966   Hauptschein et al............. 260/539

FOREIGN PATENTS OR APPLICATIONS 1,916,669   5/1970   Germany............. 260/539
1,121,040   1/1962   Germany............. 260/539
44-7691   11/1969   Japan.................. 260/539

OTHER PUBLICATIONS

Hauptschein, et al., J. Am Chem. Soc., Vol. 82, pp. 2868–2871 (1960).
Progress in Organic Chemistry, J. W. Cook, Ed., Vol. 2, pp. 47–50 (1953).

*Primary Examiner*—Vivian Garner
*Attorney, Agent, or Firm*—Joseph G. Kolodny; Prabodh I. Almaula; Edward McC. Roberts

[57] ABSTRACT

A new process for the manufacture of perfluoroalkyl-methylenecarboxylic acids of the formula $R_f(CH_2CF_2)_{m-1}CH_2COOH$, 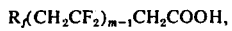

wherein $R_f$ is an unbranched or branched perfluoroalkyl radical with 3 to 14 carbon atoms and $m$ is 1 to 3, which comprises reacting perfluoroalkyl iodides of the formula $R_f(CH_2CF_2)_m$-I with concentrated nitric acid. The compounds are e.g. useful as intermediates for the manufacture of oil- and water repellents; further they can be used themselves e.g. as surface active assistants or as lubricants.

12 Claims, No Drawings

PROCESS FOR THE MANUFACTURE OF PERFLUOROALKYLMETHYLENE-CARBOXYLIC ACIDS

U.S. Pat. No. 3,255,228 teaches the manufacture of perfluoroalkylmethylenecarboxylic acids according to the following reaction equations:

$$CF_3CF_2CF_2CH_2CF_2I + ClSO_3H \rightarrow CF_3CF_2CF_2CH_2CF_2OSO_2Cl + HI$$

$$CF_3CF_2CF_2CH_2CF_2OSO_2Cl + 3H_2O \rightarrow CF_3CF_2CF_2CH_2COOH + H_2SO_4 + 2HF + HCl$$

This process leads to a poor conversion of the iodide into the desired acid and, moreover, to the occurence of difficulty identifiable by-products. The recovery of iodine ($I_2$) from the reaction mixture is only possible by means of an additional oxidation step.

The manufacture of perfluoroalkylmethylenecarboxylic acids by direct reaction of the perfluoroalkyl iodides with an acid, e.g. nitric acid, is not possible with compounds of the type $R_fCF_2I$ ($R_f$ = perfluoroalkyl radical). But on the other hand, stable nitrates of the formulae $R_f(CH_2)_n ONO_2$ and $R_f(CH_2CF_2)_n$-$CH_2CH_2ONO_2$, are obtained by reacting compounds of the formulae $R_f(CH_2)_nI$ and $R_f(CH_2CF_2)_nCH_2CH_2I$ with nitric acid (German Offenlegungsschrift 2.028.459.)

The invention is based on the surprising observation that perfluoroalkylmethylenecarboxylic acids of the formula $R_f(CH_2CF_2)_{m-1}CH_2COOH$ are obtained in good yields by reacting perfluoroalkyl iodides of the formula $R_f(CH_2CF_2)_mI$ with concentrated nitric acid.

The present invention therefore provides a process for the manufacture of perfluoroalkylmethylenecarboxylic acids of the formula $$R_f-(CH_2CF_2)_{m-1}-CH_2-COOH, \qquad (1)$$

wherein $R_f$ is an unbranched or a branched perfluoroalkyl radical with 3 to 14 carbon atoms, and $m$ is 1 to 3, which comprises reacting perfluoroalkyl iodides of the formula $$R_f-(CH_2CF_2)_m-I \qquad (2)$$

with concentrated nitric acid.

The perfluoroalkyl iodides of the formula (2) are advantageously obtained by reaction of perfluoroalkyl iodides of the formula $R_fI$ with vinylidene fluoride in the presence of catalysts.

The perfluorinated hydrocarbon radical can be a branched or, preferably, a straight-chain perfluoroalkyl radical with 3 to 14 carbon atoms and can have e.g. the following formulae:

| | |
|---|---|
| $F(CF_2)_p-$ | $p = 3$ to $13$ |
| $(CF_3)_2CF(CF_2)_q-$ | $q = 1$ to $11$ |
| $CF_3[CF_2CF(CF_3)]_r-$ | $r = 1$ to $4$ |
| $(CF_3)_2CF[CF_2CF(CF_3)]_s-$ | $s = 1$ to $4$. |

It is advantageous to use also mixtures of perfluoroalkyl iodides with different chain lengths.

It is particularly advantageous to use perfluoroalkyl iodides of the formulae $$C_nF_{2n+1}(CH_2CF_2)_mI, \qquad (3)$$

$$C_nF_{2n+1}CH_2CF_2I, \qquad (4)$$

$$C_{n_1}F_{2n_1-1}(CH_2CF_2)_mI \qquad (5)$$

and $$C_{n_1}F_{2n_1-1}CH_2CF_2I, \qquad (6)$$

wherein $n$ is a whole number from 3 to 12, $n_1$ is a whole number from 3 to 10, preferably 4 to 9, and $m$ is 1 to 3, preferably 1 and 2.

The perfluoroalkylmethylenecarboxylic acids obtained from these iodides by reaction with concentrated nitric acid then have the formulae $$C_nF_{2n+1}(CH_2CF_2)_{m-1}CH_2COOH, \qquad (3a)$$

$$C_nF_{2n+1}CH_2COOH, \qquad (4a)$$

$$C_{n_1}F_{2n_1-1}(CH_2CF_2)_{m-1}CH_2COOH \qquad (5a)$$

and $$C_{n_1}F_{n_1+1}CH_2COOH, \qquad (6a)$$

wherein $n$, $n_1$ and $m$ have the indicated meanings.

Particularly preferred also are the iodides of the formulae $$CF_3(CF_2)_3CH_2CF_2I, \qquad (7)$$

$$CF_3(CF_2)_5CH_2CF_2I, \qquad (8)$$

$$CF_3(CF_2)_7CH_2CF_2I \qquad (9)$$

and $$CF_3(CF_2)_9CH_2CF_2I, \qquad (10)$$

which are used in the reaction separately or also in admixture and which lead to the corresponding perfluoroalkylmethylenecarboxylic acids.

Concentrated nitric acid of about 90 to 98% strength is used for the reaction, which is carried out at temperature of 50°C to 150°C, preferably at 80°C to 120°C. The molar ratio or perfluoroalkyl iodide to nitric acid can be about 1:1 to 1:10, preferably 1:1 to 1:5.

The reaction can be carried out either by combining the perfluoroalkyl iodide and the nitric at room temperature and heating them jointly to the reaction temperature, or by initially heating the perfluoroalkyl iodide to reaction temperature and adding the nitric acid in small amounts to the resulting melt.

Optionally, it is also possible to carry out the reaction in solvents, e.g. aromatic solvents, such as benzene, toluene or xylene, or fluorinated solvents, such as hexafluoroisopropanol or tetrafluoropropanol.

The reaction time can be about 1 to 20 hours and as a rule increases with increasing molecular weight of the perfluoroalkyl iodide.

Upon termination of the reaction, the reaction mixture can be processed by taking it up in an ice/water mixture and subsequently extracting the aqueous solution with ethers, e.g. diethyl ether. The solvent is then removed to yield the perfluoroalkylmethylenecarboxylic acids, which, depending on the size of the molecule, are liquid or solid.

The perfluoroalkylmethylenecarboxylic acids manufactured in this way are valuable starting materials for the manufacture of oil and water repellents for compounds providing a soil-release and antisoiling finish, and for tne manufacture of tentsides, lubricants and the like. These end products are obtained e.g. by modification of the carboxyl group by known chemical reactions. In addition, they can themselves be used as surface-active assistants or lubricants.

The following Examples illustrate the invention without implying any limitation thereof.

EXAMPLE 1

100 ml of fuming 98% nitric acid are added slowly at 100°C to 82 g of perfluoroalkyl iodide of the formula $CF_3(CF_2)_n(CH_2CF_2)_oI$ ($n = 5, 7, 9$, and $o = 1, 2$. Upon completion of the addition, the reaction mixture is kept for a further 5 hours at 100°C.

The reaction mixture is then cooled and poured on 500 g of ice. The resulting aqueous solution is extracted 3 times with 200 ml of ether on each occasion. The ether is dried over sodium sulphate and distilled off.

Yield: 58:.0 g Acid titer: 710.6 mg of NaOH/g of acid, based on $C_8F_{17}CH_2COOH$.

Mass spectrum:

|  | $CF_3(CF_2)_nCH_2COOH$ | | |
|---|---|---|---|
| n = 5 | M = 378 | M-H = 377 | M-OH = 361 |
| n = 7 | M = 478 | M-H = 477 | M-OH = 461 |
| n = 9 | M = 578 | M-H = 577 | M-OH = 561 |
|  | $CF_3(CF_2)_nCH_2CF_2CH_2COOH$ | | |
| n = 5 | M = 442 | M-H = 441 | M-OH = 425 |
| n = 7 | M = 542 | M-H = 541 | M-OH = 525 |

EXAMPLE 2 (Comparison Example)

In accordance with the instructions of U.S. Pat. No. 3,255,228, 193 g of $CF_3(CF_2)_n(CH_2CF_2)_oI$ $n = 5, 7, 9$; $o = 1, 2$) are stirred with 117 g of chlorosulphonic acid over the course of 8 hours at 102°C.

The reaction product is then poured on 500 g of ice and the resulting aqueous solution is extracted with 500 ml of diethyl ether. The ether is dried over sodium sulphate and distilled off.

Yield: 50.6 g Acid titer: 250.8 mg of NaOH/g of acid, based on $C_8F_{17}CH_2COOH$.

The yield is consequently only about 36% of that according to Example 1.

I claim:

1. A process for the manufacture of perfluoroalkylmethylenecarboxylic acids of the formula $$R_f(CH_2CF_2)_{m-1}-CH_2-COOH$$

wherein $R_f$ is an unbranched or a branched perfluoroalkyl radical with 3 to 14 carbon atoms and $m$ is 1 to 3, which comprises the steps of, (a) reacting perfluoroalkyl iodides of the formula $$R_f-(CH_2CF_2)_m-I$$

with nitric acid of 90 to 98% strength in a molar ratio of iodides to nitric acid of 1:1–10, at temperatures of 50° to 150°C and a reaction time of 1 to 20 hours and (b) recovering said perfluoroalkylmethylenecarboxylic acids from the reaction mixture.

2. A process according to claim 1 for the manufacture of perfluoroalkylmethylenecarboxylic acids of the formula $$C_nF_{2n+1}-(CH_2CF_2)_{m-1}CH_2COOH.$$

wherein $n$ is a whole number from 3 to 12 and $m$ is 1 to 3, wherein the perfluoroalkyl iodides are of the formula $$C_nF_{2n+1}(CH_2CF_2)_mI$$

3. A process according to claim 2, wherein the perfluoroalkyl iodides are of the formula $$C_nF_{2n+1}-CH_2CF_2-I$$

wherein $n$ is a whole number from 3 to 12.

4. A process according to claim 2, wherein the perfluoroalkyl iodides are of the formula $$C_{n_1}F_{2n_1}-(CH_2CF_2)_mI$$

wherein $n_1$ is a whole number from 3 to 10, and $m$ is 1 to 3.

5. A process according to claim 4, wherein the perfluoroalkyl iodides are of the formula $$C_{n_1}F_{2n_1-1}-CH_2CF_2-I$$

wherein $n_1$ is a whole number from 3 to 10.

6. A process according to claim 5, wherein the reaction is carried out at 80°C to 120°C.

7. A process according to claim 6 wherein the molar ratio of iodide to nitric acid is 1:1 to 1:5.

8. A process according to claim 1 wherein the nitric acid is added to the perfluoroalkyl iodide which has been heated to the reaction temperature.

9. A process accroding to claim 1 wherein the nitric acid and the perfluoroalkyl iodide are combined at room temperature and then heated to the reaction temperature.

10. A process according to claim 1, wherein the perfluoroalkyl iodides are of the formula $$C_{n_1}F_{2n_1-1}-(CH_2CF_2)_mI$$

wherein $n_1$ is a whole number from 4 to 9.

11. A process according to claim 10, wherein the perfluoroalkyl iodides are of formula $$C_{2_1}F_{2n_1-1}-(CH_2CF_2)_mI$$

wherein $m$ is 1 or 2.

12. A process according to claim 11, wherein the perfluoroalkyl iodides are of the formula $$C_{n_1}F_{2n_1-1}-CH_2CF_2-I$$

wherein $n_1$ is a whole number from 4 to 9.

* * * * *

UNITED STATES PATENT AND TRADEMARK OFFICE
CERTIFICATE OF CORRECTION

PATENT NO. : 3,954,817
DATED : May 4, 1976
INVENTOR(S) : HORST JÄGER

It is certified that error appears in the above-identified patent and that said Letters Patent are hereby corrected as shown below:

Column 4, claim 4, line 20, the formula should read as follows:

$$C_{n_1}F_{2n_1+1}-(CH_2CF_2)_mI$$

Column 4, claim 5, line 25, the formula should read as follows:

$$C_{n_1}F_{2n_1+1}-CH_2CF_2-I$$

Column 4, claim 9, line 34, delete "accroding" and substitute --- according ---

Column 4, claim 11, line 44, insert after "of" --- the ---; line 45, delete the formula and insert --- $$C_{n_1}F_{2n_1+1}-(CH_2CF_2)_mI$$ ---.

Column 4, claim 12, line 50, the formula should read as follows:

$$C_{n_1}F_{2n_1+1}-CH_2CF_2-I$$

Signed and Sealed this

Thirty-first Day of August 1976

[SEAL]

Attest:

RUTH C. MASON
*Attesting Officer*

C. MARSHALL DANN
*Commissioner of Patents and Trademarks*